(12) United States Patent
Laub et al.

(10) Patent No.: US 8,795,671 B2
(45) Date of Patent: Aug. 5, 2014

(54) SUBCUTANEOUS ADMINISTRATION OF ANTI-HEPATITIS B ANTIBODIES

(75) Inventors: Orgad Laub, Tel-Aviv (IL); Nadav Orr, Mazkeret Batia (IL)

(73) Assignee: Omrix Biopharmaceuticals Ltd., Nes-Ziona (IL)

( * ) Notice: Subject to any disclaimer, the term of this patent is extended or adjusted under 35 U.S.C. 154(b) by 729 days.

(21) Appl. No.: 12/630,433

(22) Filed: Dec. 3, 2009

(65) Prior Publication Data

US 2010/0143378 A1  Jun. 10, 2010

Related U.S. Application Data

(60) Provisional application No. 61/119,827, filed on Dec. 4, 2008.

(51) Int. Cl.
*A61K 39/395* (2006.01)
*A61P 31/12* (2006.01)

(52) U.S. Cl.
USPC .......................................... 424/161.1; 435/5

(58) Field of Classification Search
None
See application file for complete search history.

(56) References Cited

U.S. PATENT DOCUMENTS

| | | | |
|---|---|---|---|
| 6,468,733 | B2 | 10/2002 | Nur et al. |
| 2005/0260195 | A1 | 11/2005 | Dagan et al. |
| 2007/0037170 | A1 | 2/2007 | Nur et al. |

FOREIGN PATENT DOCUMENTS

| | | |
|---|---|---|
| EP | 1161958 A1 | 12/2001 |
| WO | 9918130 A1 | 4/1999 |
| WO | 2007017859 A1 | 2/2007 |

OTHER PUBLICATIONS

Powell et al. (Clinical Transplantation, 2006, vol. 4, p. 524-525 in IDS on Mar. 4, 2010).*
Smith et al. (The Lancet, 1972, vol. 1, p. 1208-1212).*
Moore and Quinn (Annals of Allergy, Asthma and Immunology, Aug. 2008, vol. 101, p. 114-121 in IDS on Mar. 4, 2010).*
Alonso et al., "Effectiveness of low-dose intramuscular anti-VHB immune globulin in the prophylaxis of viral B hepatitis reinfection after liver transplantation: preliminary report," Transplant Proc., 2003, pp. 1850-1851, vol. 35.
Faust et al., "Cost-effective and safe ambulatory long-term immunoprophylaxis with intramuscular instead of intravenous hepatitis B immunoglobulint to prevent reinfection after orthotopic liver transplantation," Clin. Transplant, 2003, pp. 254-258, vol. 17.
Filipponi et al., "Efficacy, Safety and Pharmacokinetics of Intramuscular Hepatitis B Immune Globulin, Igantibee®, for the Prophylaxis of Viral B Hepatitis after Liver Transplantation," Dig Liver Dis, 2009.
Hooman et al., "Antibody to Hepatitis B Surface Antigen Trough Levels and Half-Lives Do Not Differ After Intravenous and Intramuscular Hepatitis B Immunoglobulin Administration After Liver Transplantation," Liver Transpl., 2008, pp. 435-442, vol. 14.
Moore et al., "Subcutaneous Immunoglobulin Replacement Therapy for Primary Antibody Deficiency: Advancements into the 21st Century," Annals of Allergy, Asthma & Immunology, 2008, pp. 114-121, vol. 101, No. 2.
Ochs et al., "Safety and Efficacy of Self-Administered Subcutaneous Immunoglobulin in Patients with Primary Immunodeficiency in Patients with Primary Immunodeficiency Diseases," Journal of Clinical Immunology, 2006, pp. 265-273, vol. 26, No. 3.
Powell et al., "Subcutaneous Administration of Hepatitis B Immune Globulin in Combination with Lamivudine Following Orthotopic Liver Transplantation: Effective Prophylaxis Against Reccurrence," Clin Transplant, 2006, pp. 524-525, vol. 20.
Ringe et al., "A Novel Management Strategy of Steroid-Free Immunosuppression After Liver Transplantation: Efficacy and Safety of Tacrolimus and Mycophenolate Mofetil," Transplantation, 2001, pp. 508-515, vol. 71.
Stiehm et al., "Preparation and Use of Therapeutic Antibodies Primarily of Human Origin," Biologicals, 2008, pp. 363-374, vol. 36.
Thurmann et al., "Pharmacokinetics and Safety of a Novel Anti-HBs-Enriched Immunoglobulin in Healthy Volunteers After Subcutaneous and Intramuscular Administration," European Journal of Clinical Pharmacology, 2006, pp. 511-512, vol. 62, No. 7.
Yao et al., "Intramuscular Hepatitis B Immune Globulin Combined with Lamivudine for Prophylaxis Against Hepatitis B Recurrence After Liver Transplantation," Liver Transpl Surg, 1999, pp. 491-496, vol. 5.
Yoshida et al., "Liver Transplantation for Chronic Hepatitis B Infection with the Use of Combination of Lamivudine and Low-Dose Hepatitis B Immune Globulin," Liver Transpl Surg, 1999, pp. 520-525, vol. 5.
World Health OrganizationFact Sheet No. 204, Aug. 2008.
EP09156525 European Search Report dated Oct. 7, 2009.

* cited by examiner

*Primary Examiner* — Agnieszka Boesen
(74) *Attorney, Agent, or Firm* — Browdy and Neimark, PLLC

(57) ABSTRACT

The present application relates to an immunoglobulin preparation comprising anti-hepatitis B antibodies for subcutaneous administration and to uses thereof, including methods for treating, preventing and/or reducing a disease, disorder or condition associated with hepatitis B virus.

16 Claims, 2 Drawing Sheets

SUBCUTANEOUS ADMINISTRATION OF ANTI-HEPATITIS B ANTIBODIES

The present application claims the benefit of U.S. provisional application No. 61/119,827, filed Dec. 4, 2008, the entire contents of which are hereby incorporated by reference.

FIELD OF THE INVENTION

The present invention relates to an immunoglobulin preparation comprising anti-hepatitis B antibodies for subcutaneous administration and to uses thereof.

BACKGROUND OF THE INVENTION

Hepatitis B is a potentially life-threatening liver infection caused by the Hepatitis B virus (HBV). HBV infection can result in acute hepatitis (clinically apparent) or in a chronic disease. The clinical manifestations of acute infection include yellowing of the skin and eyes (jaundice); extreme fatigue; dark urine; nausea; diarrhea and vomiting; loss of appetite; and muscles, joints or abdominal pain. About 1-2% of individuals suffering from acute hepatitis B die from fulminant hepatic failure. Chronic HBV infection can stay undetected in the body for decades before it leads to an end-stage liver disease, including cirrhosis (scarring of the liver) and hepatocellular carcinoma.

HBV infection has a worldwide distribution. It is estimated that more than 2 billion of the global population has been infected with Hepatitis B virus (HBV). Of these, approximately 350 million have chronic liver infection and are at risk of serious illness and death from cirrhosis and hepatocellular carcinoma [World Health Organization; Fact sheet No. 204; August 2008].

Humans are the only reservoir of HBV. The virus is extremely contagious and is transmitted by percutaneous and mucosal exposure to blood or other body fluids of an infected person. Common modes of transmission may include mother-to-infant (perinatal), use of contaminated needles, contaminated blood transfusions and via unprotected sexual contact with an infected person. In addition, HBV is the major infectious occupational hazard of health workers, and most health care workers receive hepatitis B vaccine.

Advanced cases of viral caused hepatitis result in liver failure and orthotopic liver transplantation (OLT) is the only curative treatment. OLT refers to a procedure in which an impaired liver is removed from the patient's body and a healthy donor's liver is transplanted instead. However, although the diseased liver is removed, circulating virus may remain in the serum of the patient and in other body compartments; invade and infect the grafted liver; and consequently cause hepatitis recurrence. Thus, preventing HBV infection of the grafted liver is essential to avoid recurrence of hepatitis and crucial for maintaining liver function in OLT patients.

Passive immunization with Hepatitis B immunoglobulin (HBIG) has been shown to markedly reduce the incidence of Hepatitis B recurrence after liver transplantation and is now a well established approach used in OLT patients (Filipponi et al "Efficacy, safety, and pharmacokinetics of intramuscular hepatitis B immune globulin, Igantibe®, for the prophylaxis of viral B hepatitis after liver transplantation". Dig Liver Dis. 2009). HBIG is derived from blood plasma of human donors expressing high titers of antibodies specific against hepatitis B surface antigen (anti-HBsAg). The antibodies bind to the surface antigen of the virus; inactivate circulating viruses; and prevent subsequent infection.

Immunoglobulin can be administrated in one of the following routes: intravenously (IV), intramuscularly (IM) or subcutaneously (SC).

Moore and Quinn ("Subcutaneous immunoglobulin replacement therapy for primary antibody deficiency: advancements into the 21st century". Ann Allergy Asthma Immunol. 2008; 101:114-121) provide a review on subcutaneous immunoglobulin therapy for patients with primary antibody deficiency (PAD). In their report it is indicated that immunoglobulin injected into the subcutaneous tissue has reduced intravenous bioavailability secondary to IgG catabolism and incomplete absorption from the subcutaneous space into the intravascular space. On the one hand according to US recommendations when transitioning from intravenous immunoglobulin (IVIG) to subcutaneous immunoglobulin (SCIG) therapy in patients with PAD the monthly IVIG dose is increased by 37% and divide by 4 to determine the weekly SCIG dose. The product is infused in multiple sites simultaneously with a total volume of up to 25 ml per infusion site. On the other hand dosing recommendations in European countries consists on a 1:1 dose conversion between WIG and SCIG infusions. It was also reported by Ochs et al ("Safety and efficacy of self-administered subcutaneous immunoglobulin in patients with primary immunodeficiency diseases". J Clin Immunol. 2006; 26:265-273) that the average increase of the SCIG dose to 137% of that given intravenously dose is unnecessary and does not appear to confer any additional benefits in patients with primary immune deficiency diseases (PIDD).

In OLT patients, HBIG is typically administered by intravenous route concurrently with the grafting of the transplanted liver (the anhepatic phase), with subsequent daily dosing during each of the first 7 days post-transplantation. In the extended post-transplant period HBIG is administered monthly on an indefinite basis.

Most of the licensed immunoglobulin preparations are for intramuscular use (Stiehm et al. "Preparation and use of therapeutic antibodies primarily of human origin". Biologicals. 2008; 36:363-374). The following are some of the commercially available HBIG formulations which are indicated for intravenous or intramuscular administration:

Omri-Hep-B™ (manufactured by Omrix Biopharmaceuticals) is prepared from human plasma collected from healthy anti-HBsAg high titer donors. Omri-Hep-B™ is used for passive immunization in the prevention of hepatitis B recurrence after liver transplantation. Omri-Hep-B™ is a sterile solution containing 5% protein of which at least 95% is human immunoglobulin G, 50 IU/ml of antibodies to HBsAg as the active ingredient, 10% maltose and water for injection. Omri-Hep-B™ is administered by intravenous infusion. HepaGam B™ (manufactured by Cangene Corporation) is indicated for the prevention of hepatitis B recurrence following liver transplantation, in HBsAg positive liver transplant patients. It is prepared from selected plasma donated by healthy, vaccinated and anti-HBsAg high titer donors. HepaGam B™ is formulated as a 5% (50 mg/mL) protein solution with 10% maltose and 0.03% polysorbate 80 at pH 5.6. It is available in 1 ml and 5 ml single dose vials containing about 312 IU/ml anti-HBsAg. HepaGam B™ is administered intravenously.

Hepatec® (manufactured by Biotest Pharma GmbH) is a human hepatitis B immunoglobulin solution for intravenous administration. 1 ml Hepatec® contains: 100 mg human plasma protein (10% protein) of which at least 95% is immunoglobulin G, 50 IU of antibodies to HBsAg, sodium chloride and water for injection.

HyperHEP B™ (manufactured by Talecris Biotherapeutics Inc.) is a solution which contains high quantities of anti-hepatitis B immune globulin for intramuscular administration. HyperHEP B™ is prepared from the plasma of healthy vaccinated anti-HBsAg high titer donors. It is formulated as a 15-18% protein solution at a pH of 6.4-7.2 in 0.21-0.32 M glycine. The formulation contains about 220 IU per ml anti-HBsAg. BayHep B® (distributed by Bayer New Zealand Limited) is a hepatitis B immunoglobulin solution for intramuscular injection. 1 ml contains 217 IU anti-hepatitis B antibodies and 19.5 mg glycine. It is available in 0.5 ml neonatal single dose syringe, and 1 ml single dose vial.

Nabi-HB® (manufactured by Nabi® Biopharmaceuticals) is a sterile solution of immunoglobulin (5±1% protein) containing antibodies to hepatitis B surface antigen (anti-HBs). It is prepared from plasma donated by individuals with high titers of anti-HBs. Nabi-HB is formulated in 0.075 M sodium chloride, 0.15 M glycine, and 0.01% polysorbate 80, at pH 6.2. It contains 312 IU/ml anti-HBs and it is intended for administration in the intramuscular route.

According to the leaflet HyperHEP B™, BayHep B® and Nabi-HB® are indicated for acute exposure to blood containing HBsAg; perinatal exposure of infants born to HBsAg-positive mothers; sexual exposure to an HBsAg-positive person; and household exposure to persons with acute HBV infection.

Igantibe® (manufactured by Grifols) is a human anti-hepatitis B immunoglobulin for intramuscular use. Igantibe® is obtained from immunized plasma donors. The product contains 200 IU/ml with an IgG content of higher than 95% and HBIG content of 15.3%. It is formulated with glycine (2.25%), sodium chloride (0.30%) and sterile water for injection.

Various IV and/or IM dosing regimes of HBIG optionally combined with an anti-viral drug such as lamivudine are reported for OLT subjects.

Filipponi et al (2009) reported administration of Igantibe®, a specific HBIG (manufactured by Grifols), to adult patients who underwent liver transplantation more than 18 months earlier. IM administration of 2000 IU Igantibe® was carried out once every 14 days namely bimonthly for a period of 6 months. This regime allowed anti-HBs levels of ≥150 IU/L in the circulation of the subjects throughout the study period. In another study, Igantibe® was administered IM to OLT patients in a one monthly dose of 2000 IU and the HBV antibody titer were measured every month. This regime attained a protective antibody titer of >100 IU/L in the circulation for at least the first year after transplantation (Alonso et al. "Effectiveness of low-dose intramuscular anti-VHB immune globulin in the prophylaxis of viral B hepatitis reinfection after liver transplantation: preliminary report". Transplant Proc. 2003; 35:1850-1851). Both regimes (i.e. bimonthly and monthly administration) were considered protective and efficacious in prophylaxis of viral B hepatitis after liver transplantation.

Also, Faust et al. ("Cost-effective and safe ambulatory long-term immunoprophylaxis with intramuscular instead of intravenous hepatitis B immunoglobulin to prevent reinfection after orthotopic liver transplantation". Clin Transplant. 2003; 17:254-258) reported that administration of 2000 IU IM HBIG given once a month together with 100 mg lamivudine per day is effective in prophylaxis of HBV re-infection in patients after OLT.

Yao et al. ("Intramuscular hepatitis B immune globulin combined with lamivudine for prophylaxis against hepatitis B recurrence after liver transplantation". Liver Transpl Surg. 1999; 5:491-496) described a protocol comprising administration of IM HBIG and oral lamivudine (150 mg/d) in patients with HBV infection who underwent OLT. Patients with detectable HBV DNA at the time of OLT received 10,000 U (45 ml) of IV HBIG daily for 7 days, followed by 5 ml of IM HBIG weekly for the next 3 weeks, then every 3 weeks. Patients who were HBV DNA negative received on dose of IV HBIG (45 ml) during surgery, followed by 5 ml IM HBIG weekly for 4 weeks, then every 3 weeks. During a follow up of 15.6 months, all patients developed protective anti-HBs titers greater than 200 IU/L in the circulation and had no evidence of HBV recurrence.

Yoshida et al ("Liver transplantation for chronic hepatitis B infection with the use of combination lamivudine and low-dose hepatitis B immune globulin". Liver Transpl Surg. 1999; 5:520-5.) studied the effectiveness of a post-transplantation prophylaxis protocol using a combination of lamivudine and HBIG in patients with chronic HBV infection. In the maintenance period HBIG therapy consisted of 2170 IU intramuscularly twice weekly, tapered to every 2 to 4 weeks by 12 months post-transplantation. Target serum HBIG titers were less than 500 IU/L for the first 6 months after OLT and then greater than 300 IU/L within the following 6 months. All patients achieved the target HBIG titer and allograft re-infection by HBV was prevented.

Using subcutaneous administration of immunoglobulin has several advantages. For example, subcutaneous IG infusions are well tolerated compared to IM administration, safe, and give the patient more independence compared to IV administration.

The reported dose for subcutaneous HBIG administration is similar or lower than that of intramuscular administration.

Subcutaneous administration of hepatitis B immunoglobulin (HBIG) in combination with lamivudine was previously reported (Powell et al. ("Subcutaneous administration of hepatitis B immune globulin in combination with lamivudine following orthotopic liver transplantation: effective prophylaxis against recurrence". Clin Transplant. 2006; 20:524-525). According to the report the disclosed HBIG contained an antibody titer of 217 IU/ml anti-HBsAg and a regime of multiple daily injections (four aliquots of 2.5 ml) was applied via the subcutaneous route for seven days following the liver transplantation. Maintenance subcutaneous dosing of 2170 IU was administered every three weeks achieving serum anti-HBs titers from 500 to 1000 IU/L over five months post transplant.

The following reports show pharmacokinetic parameters of subcutaneous HBIG vis a vis intramuscular administration.

Thürmann et al. ("Pharmacokinetics and safety of a novel anti-HBs-enriched immunoglobulin in healthy volunteers after subcutaneous and intramuscular administration". Eur J Clin Pharmacol. 2006; 62:511-512) investigated the pharmacokinetics of an anti-HBsAg-enriched immunoglobulin preparation which contains 635 IU anti-HBsAg/ml. The immunoglobulin was administered in an equal single dose of 30 IU/kg body weight either subcutaneously or intramuscularly. According to the paper comparable serum concentrations were obtained using both subcutaneous and intramuscular administration routes. Additionally, the bioavailability of the investigated HBIG preparation following subcutaneous and intramuscular administration was comparable to that following intravenous administration.

In a recent study Hooman et al. ("Antibody to hepatitis B surface antigen trough levels and half-lives do not differ after intravenous and intramuscular hepatitis B immunoglobulin administration after liver transplantation". Liver Transpl. 2008; 14:435-442) compared pharmacokinetic parameters after IM and IV administration of 2000 IU HBIG. According to the report, although the area under the curve (AUC) levels were not measured during the first two weeks after HBIG administration, it was presumed that they were lower in IM as compared to IV administration. It is also indicated that the principles of pharmacokinetic parameters after SC administration are expected to be similar to IM administration. The report is silent on the levels of anti-HBs present in the circulation during the first two weeks following the different administration routes.

Recently (September 2009), the European Committee for Medical Products for Human Use (CHMP) recommended the granting of a marketing authorization for Zutectra®, a human hepatitis B immunoglobulin solution for subcutaneous administration. Zutectra® is manufactured from plasma of donors with high anti-HBs antibody titers (Biotest Pharma GmbH) and is intended for the prevention of hepatitis B virus re-infection after liver transplantation. It is available in 1 ml pre-filled syringe containing 500 IU anti-HBs antibodies. It is reported that effective anti-HBs-serum levels are achieved with weekly Zutectra® application.

SUMMARY OF THE INVENTION

Administration of hepatitis B immunoglobulin (HBIG) reduces the frequency and severity of hepatitis B virus (HBV) infection. In this regard, maintaining adequate levels of anti-hepatitis B antibodies in the circulation of a subject in need is highly desired.

Advanced cases of viral caused hepatitis result in liver failure and orthotopic liver transplantation (OLT) is the only curative treatment. OLT refers to a procedure in which an impaired liver is removed from the patient's body and a healthy donor's liver is transplanted instead. However, although the diseased liver is removed, circulating virus may remain in the serum of the patient and in other body compartments; invade and infect the grafted liver; and consequently cause hepatitis recurrence. Thus, preventing HBV infection of the grafted liver is essential to avoid recurrence of hepatitis and crucial for maintaining liver function in OLT patients.

Passive immunization with intravenous Hepatitis B immunoglobulin (HBIG) has been shown to markedly reduce the incidence of Hepatitis B recurrence after liver transplantation and is now a well established approach used in OLT patients.

To prevent or minimize HBV recurrence in patients who have undergone orthotopic liver transplantation, HBIG therapy is required on a lifelong basis. Oftentimes, HBIG is administered via the intravenous or intramuscular route. In some cases the intravenous formulation is used intramuscularly.

Using subcutaneous therapy for these patients offers several advantages over the two other routes of administration.

An intravenous therapy requires administration by a trained medical personal and at times hospitalization. In contrast, in subcutaneous therapy close supervision is unnecessary, and infection is unlikely to occur. Subcutaneous therapy can be self administered at home, significantly improving the patient's quality of life.

Furthermore, following organ transplantations patients are regularly under immunosuppressive regimes (Ringe et al. "A novel management strategy of steroid-free immunosuppression after liver transplantation: efficacy and safety of tacrolimus and mycophenolate mofetil". Transplantation. 2001; 71:508-515). These immunocompromised patients are at high risk of contracting an infectious disease. Thus, avoiding prolonged intravenous drug administration and hospital admission is of great advantage.

Although intramuscular injection, as subcutaneous administration, can be self-administered, it causes significant pain at the injection site, a phenomenon which leads to poor compliance in some patients (Moore and Quinn 2008). Also, intramuscular injection may cause deep tissue complications.

The art discloses administering HBIG preparations by subcutaneous and intramuscular routes. The art does not differentiate between these two routes of administration and in some cases the intramuscular formulation/dose is used subcutaneously.

It was found according to the present invention that subcutaneous injection results in a delayed appearance of HBIG in the circulation as compared to intramuscular administration. These findings pave the way to a different treatment approach when using HBIG by the subcutaneous route. The present invention provides administration of a HBIG subcutaneous dose which is higher than the dose that is required or employed by the intramuscular route, e.g. 1.5, 2 or 2.5 folds higher.

Advantageously, the present invention provides an improved hepatitis B immunoglobulin preparation for subcutaneous administration and methods for subcutaneous administration of hepatitis B immunoglobulin.

In one aspect, the invention provides a method for subcutaneous immunoglobulin hepatitis B therapy, comprising subcutaneously administering to a subject in need a dose of anti-hepatitis B immunoglobulin that is higher than a dose of anti-hepatitis B immunoglobulin administered by the intramuscular route, thereby achieving anti-hepatitis B antibodies in the circulation at a similar level and timing as by the intramuscular route.

In one embodiment of the invention, the subject is selected from the group consisting of an orthotopic liver transplantation (OLT) patient, a newborn to a viral infected mother, and a subject exposed to the virus.

In another embodiment of the invention, the subcutaneous dose is at least 2-fold higher than the dose administered by the intramuscular route.

Yet, in another embodiment of the invention, the subcutaneous dose is higher than 2170 IU.

In a further embodiment of the invention, the subcutaneous dose is equal to or higher than 3000 IU.

In another embodiment of the invention, the subcutaneous administering is carried out by injection.

In another further embodiment of the invention, the subcutaneous administering is carried out by a single dispensation.

Yet, in another embodiment of the invention, the subcutaneous dose has a titer of anti-hepatitis B antibodies that is greater than 635 IU/ml.

Another aspect of the invention relates to a method for treating, preventing and/or reducing a disease, disorder or condition associated with hepatitis B virus, comprising administering to a subject in need thereof a dose of anti-hepatitis B immunoglobulin sufficient to obtain a predetermined level of anti-hepatitis B antibodies in the circulation of the subject, the improvement wherein the anti-hepatitis B immunoglobulin is administered by the subcutaneous route in a dose that is at least 1.5 times higher than the intramuscular formulated dose needed to obtain said predetermined level of anti-hepatitis B antibodies in the circulation of the subject, wherein the predetermined level is obtained in the circulation by the subcutaneous dose at a similar timing as in the intramuscular formulated dose.

In one embodiment of the invention, the predetermined level of anti-hepatitis B antibodies in the circulation is greater than 100 mIU/ml.

In another embodiment of the invention, the timing is before the third, second or first day following subcutaneous administration.

In still another embodiment of the invention, the subcutaneous administration is carried out by injection.

In yet another embodiment of the invention, the subcutaneous administration is carried out by a single dispensation.

In yet another embodiment of the invention, the subject was previously treated by a dosing regimen of intravenous administration of anti-hepatitis B immunoglobulin.

In another embodiment of the invention, the subcutaneous dose has a titer of anti-hepatitis B antibodies that is greater than 635 IU/ml.

Another object of the invention is to provide a method for preventing hepatitis B viral infection recurrence in a subject who underwent orthotopic liver transplantation (OLT), comprising administering to the subject a dose of anti-hepatitis B immunoglobulin sufficient to obtain a predetermined level of anti-hepatitis B antibodies in the circulation of the subject, the improvement wherein the anti-hepatitis B immunoglobulin is administered by the subcutaneous route in a dose that is at least 1.5 times higher than the intramuscular formulated dose needed to obtain a similar level of anti-hepatitis B antibodies in the circulation of the subject, wherein the predetermined level is obtained in the circulation by the subcutaneous dose at a similar timing as in the intramuscular formulated dose.

In one embodiment of the invention, the subcutaneous administering is carried out by injection.

In another embodiment of the invention, the subcutaneous administering is carried out by a single dispensation.

A further aspect of the invention is to provide a method for treating, preventing and/or reducing a disease, disorder or condition associated with hepatitis B virus in a subject in need thereof, the method comprising a first dosing regimen of intramuscular administration of anti-hepatitis B immunoglobulin, followed by a second dosing regimen, which comprises subcutaneously administering to the subject a dose of anti-hepatitis B immunoglobulin that is higher than the dose employed by the first dosing regimen of intramuscular administration, thereby obtaining anti-hepatitis B antibodies in the circulation of the subject at a similar level and timing as in the first dosing regimen of intramuscular administration.

In one embodiment of the invention, the timing is before the third, second or first day following subcutaneous administration.

BRIEF DESCRIPTION OF THE DRAWINGS

The features, aspects, and advantages of the present invention will become better understood with regard to the following description, examples, claims, and the following figures.

DETAILED DESCRIPTION OF THE INVENTION

Figure 1:
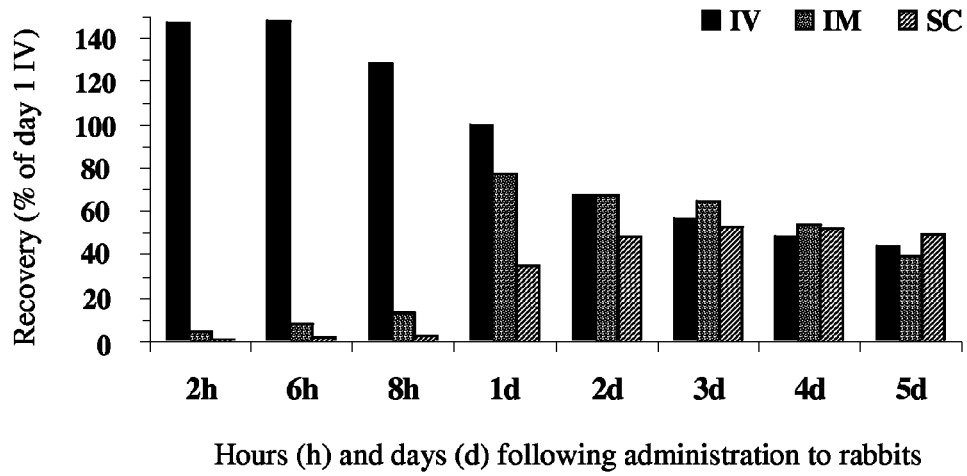
FIG. 1: shows the recovery of anti-hepatitis B antibodies in rabbit's blood following administration of Hepatitis B immunoglobulin (HBIG). The immunoglobulin was administered by intravenous (IV), intramuscular (IM) or subcutaneous (SC) route. The level of antibodies on day one following IV administration was assigned as a reference value (100%).

The present invention provides methods for subcutaneous administration of hepatitis B immunoglobulin and an improved hepatitis B immunoglobulin preparation for subcutaneous administration. More specifically, the present invention relates to the use of an increased subcutaneous dose of anti-hepatitis B immunoglobulin when transitioning from intramuscular to subcutaneous therapy.

In one aspect, the invention provides a method for achieving an efficient level of anti-hepatitis B antibodies in the circulation of a subject in need through subcutaneous administration. In one embodiment of the invention, the method comprises a) providing an anti-hepatitis B immunoglobulin preparation, b) administering subcutaneously to said subject the preparation of a), wherein said preparation is administered at a dose that is higher than that applied by intramuscular route.

The term "subcutaneous administration" refers to introduction e.g. by injection of the immunoglobulin preparation under the skin of an animal or human patient. The introduction of the preparation can be carried out by creating a pocket between the skin and the underlying tissue. The administration can be to the layer of fat which lies between the dermis and underlying fascia. The pocket may be created by pinching or drawing the skin up and away from underlying tissue. Places on the body where people can administer the immunoglobulin include, but are not limited to, the outer area of the upper arm, above or below the waist, the upper area of the buttock, just behind the hip bone and the front of the thigh. In one embodiment of the invention, the subcutaneous administration is carried out by injection.

Within the context of this invention the term "dose" refers to the amount of antibody given in a single administration. The term "administration", as used herein, means introduction of the immunoglobulin composition into the subject by subcutaneous administration.

The invention teaches that when transitioning from intramuscular to subcutaneous therapy with hepatitis B antibody preparation the dose needs to be adjusted accordingly. In one embodiment of the invention, the required subcutaneous dose is at least 1.5-fold, such as about 2 or 2.5 fold the intramuscular dose.

The teaching of the invention is based on results obtained according to the invention. It was surprisingly found according to the present invention that administering anti-HBsAg by the subcutaneous route results in a decreased bioavailability on the first two days following administration as compared to the intramuscular route. Also, it has been found according to the present invention that in the subcutaneous route the antibodies are slowly released into the intravascular space achieving a peak serum concentration 3 to 4 days after administration. More specifically, the results according to the invention show that intramuscular administration achieved efficient levels faster than subcutaneous administration. The term "bioavailability" refers to the fraction of an administered dose that reaches the general circulation.

These findings point toward the advantage of administering subcutaneously a higher amount of antibodies as compared to the intramuscular route to rapidly achieve efficient levels of antibodies in the circulation of the subject.

There are patients who after administration of an immunoglobulin preparation fail to achieve efficient levels of anti-HB antibodies in the circulation and patients who are particularly susceptible to extensive loss of circulated anti-hepatitis B antibodies, for example, patients who have surgical bleeding, patients having undergone abdominal fluid drainage, and patients who undergo plasmapheresis. The preparations and methods according to the invention are of cardinal importance in these patients. These patients may require a higher dose and/or more frequent injections. For example, the subcutaneous dose in these patients can be at least 2-fold, such about 2.5 or 3 fold the intramuscular dose. Also, the preparations and methods of the invention can be advantageously used in patients with poor intravenous access, patients with aseptic meningitis, patients with anaphylactic reactions to intravenous immunoglobulin, patients with rapid gastrointestinal protein loss, and immunocompromised patients such as patients following organ transplantations receiving immunosuppressive regimes and patients receiving anti-cancer treatment.

In one embodiment of the invention, the titer of the anti-hepatitis B antibodies in the immunoglobulin preparation is higher than 635 IU/ml, for example, equal to or greater than 700, 1000, 1400 or 2000 IU/ml.

Subcutaneous IgG are usually administered by continuous slow infusion using an infusion portable pump. In addition, administration of large doses is accomplished by using multiple application sites (Stiehm et al. 2008). One of the advantages of the immunoglobulin preparation of the invention is that it contains a high concentration of anti-hepatitis B antibodies which enables subcutaneous injection of the required high dose in a low volume without the need of a continuous slow infusion and/or multiple applications such as in a single dispensation. For example, the dose for an adult weighing 70 kg can be administered at a volume of equal to or less than about 4.5 ml, for example, about 3, 2, 1.5 or 1 ml.

As used herein, the term "infusion" refers to a continuous, slow introduction of fluids into the body. The term "infusion portable pump" refers to low infusion rate pressurizing devices used in administering or infusing medical fluids.

In the results according to the invention, when comparing the anti-hepatitis B antibodies in the circulation on day one following administration, it is evident that IM administration lead to about 2-fold increase in the antibody levels as compared to SC administration. The results obtained herein collected during the observation period of two weeks show that the calculated average area under the curve (AUC) in both models was similar in the SC and IM routes. Administering subcutaneously a higher amount of antibodies may increase the AUC. Employing higher amounts of antibodies can be advantageously used to obtain early adequate serum IgG levels.

Using the method according to the invention will assist to quickly obtain an adequate level of immunoglobulin in the circulation of a patient. Also, subcutaneous administration according to the invention will result in anti-hepatitis B antibodies in the circulation at a similar level and timing as the intramuscular administration. In one embodiment of the invention, the similar level is achieved before the third day following subcutaneous administration of the immunoglobulin preparation. In another embodiment of the invention, said level is reached on the second day post subcutaneous administration. Yet, in another embodiment of the invention, said level is reached one day following subcutaneous administration of the immunoglobulin preparation.

As used herein, the terms "efficient level" and "adequate level" refer to an amount of anti-hepatitis B antibodies in the circulation of an animal or human patient that is similar to the level of anti-hepatitis B antibodies following IM administration and/or that will elicit a "therapeutic response". As used herein the term "therapeutic response" means alleviating the symptoms of the HBV infection, inhibiting hepatitis recurrence in OLT patients and/or reducing the number or eliminating the hepatitis B viral particles in the circulation of the patient.

Alonso et al. (2003) reported that an antibody titer of >100 mIU/ml in the circulation is considered protective and efficacious in prophylaxis of viral B hepatitis. Accordingly, the efficient level of anti-hepatitis B antibodies in the circulation can be about or greater than 100 mIU/ml, like for example 150, 200, 300, 400 or 500 mIU/ml. In one embodiment of the invention, the level is about or greater than 100 mIU/ml. In another embodiment of the invention, the efficient level is higher than 100 mIU/ml. Obtaining quickly levels of anti-hepatitis B antibodies higher than 100 mIU/ml such as 150, 200, 250, 300 and 500 mIU/ml is of advantage in high risk OLT patients and/or in patients in which administration of antiviral agents is not possible. The term "high risk OLT patients" is for example patients with detectable HBV E antigen (HBeAg) prior to liver transplantation and/or patients who are particularly susceptible to extensive loss of circulating anti-HBs such as patients who have surgical bleeding, patients who undergo abdominal fluid drainage, and patients who undergo plasmapheresis.

The term "hepatitis B viral infection" refers to "acute hepatitis B" or "chronic HBV" infection which may develop to permanent liver damage (scarring of the liver), end-stage liver disease, and/or hepatocellular carcinoma. By "acute hepatitis B" it is meant a new symptomatic HBV infection. Symptoms and signs of the acute disease include, but are not limited to, loss of appetite, nausea, weakness, abdominal and joint pain, vomiting, jaundice (yellow eyes and skin), skin rashes and dark urine. By "chronic HBV infection" it is meant persistent i.e. long term infection with HBV. The chronic infection may be present without apparent symptoms.

According to the invention, the monthly dosage of anti-HBsAg can be more than 30 IU/kg such as 42, 70, 85, 94 IU/kg body weight. In one embodiment of the invention, the monthly dosage is about 42 IU/kg body weight. In another embodiment of the invention, the dosage per month for an adult weighing 70 kg is more than 2100 IU such as 2170 IU. Yet in another embodiment of the invention, the dosage per month for a child weighing 20 kg is more than 600 IU. Yet in another embodiment of the invention, the dosage per month for an adult weighing 70 kg is about 3000 IU. Yet in another further embodiment of the invention, the dosage per month for an adult weighing 70 kg is about 4950 IU. In another embodiment of the invention, the dosage per month for an adult weighing 70 kg is about 6000 IU.

The term "dosage" and "dosing" refers to a schedule regimen wherein one or multiple doses of the compositions are administered during a predetermined period of time. In one embodiment of the invention the period of time is one month.

The total dosage per month can be administered in one injection or can be divided to several portions and administered several times during the month while at least the initial portion is administered at a higher dose than that required by intramuscular route, such as 1.5, 2 or 2.5 folds higher. For example, the total monthly treatment can be divided to two and administered once every two weeks. In one embodiment of the invention, each subcutaneous dose is administered at a higher dose than that required by or employed with intramuscular route. In another embodiment of the invention, each subcutaneous dose is administered at a dose which is at least 1.5-folds higher than that required by or employed with intramuscular route.

In one embodiment of the invention, the immunoglobulin is administered pre or post orthotopic liver transplantation. In another embodiment of the invention, the immunoglobulin is administered for prophylaxis of hepatitis B viral infection post orthotopic liver transplantation. In the latter embodiment the immunoglobulin can be administered during the maintenance treatment period. The term "maintenance period" refers to the post-transplant time point wherein a single dose is administered at repeated intervals (referred to herein as maintenance dose) to maintain a protective level of anti-hepatitis B in the circulation and decrease the risk of viral hepatitis B recurrence. The maintenance period can refer to the early post-transplant time point such as the first seven days following the liver transplantation or the extended post-transplant period such as eight days onwards. In one embodiment of the invention, the maintenance period refers to the extended post-transplant period.

Advantageously, the IM dosing and the maintenance period have been shown in the literature and the art to achieve protective levels of anti-hepatitis B in the circulation and/or to statistically prevent hepatitis B virus re-infection in subjects who underwent orthotopic liver transplantation. According to the invention when transitioning from intramuscular to subcutaneous administration the administered dose should be increased, for example, the dose is at least 150% of that given intramuscularly. The recommended IM dose can change for a given indication, and for a desired level in the circulation (e.g. 100 vs. 500 mIU/ml). The subcutaneous dose should be increased to achieve the same pharmacokinetic characteristics as each recommended IM dose.

For example, to achieve an anti-HBs level of greater than 100 mIU/ml the immunoglobulin preparation can be administered subcutaneously once a month at a dose of 3000 IU. Alternatively, to achieve an anti-HBs level greater than 150 mIU/ml in the circulation, the immunoglobulin preparation can be administered subcutaneously bi-monthly each at a dose of 3000 IU. In another embodiment of the invention, to obtain anti-HBs titers greater than 200 mIU/ml in viremic patients (patients who are HBV DNA positive), the immunoglobulin preparation can be subcutaneously administered at a weekly dose of 1650 IU on week 2-4 post-operative and then at a dose of 1650 IU every three weeks. In another further embodiment of the invention, to obtain anti-HBs titers greater than 200 mIU/ml in HBV DNA negative patients the immunoglobulin can be administered at a dose of 1650 IU on week 1 to 4 post-operative and then every 3 weeks. In another further embodiment of the invention, the immunoglobulin preparation can be administered at a dose of 3255 IU twice weekly, followed by a dose of 3255 IU every 2 to 4 weeks by 12 months post-transplantation. Advantageously, this treatment may achieve a target serum HBIG titer of equal to or less than 500 mIU/ml in the first 6 months after OLT and then greater than 300 mIU/ml within the following 6 months.

The administered immunoglobulin preparation may optionally comprise an acceptable carrier. As used herein the term "acceptable carrier" refers to a diluent or a vehicle which is suitable for subcutaneous injection. The carrier can be selected from any of the carriers known in the art such as, but not limited to, saline, water, emulsions, sodium chloride solution, and mixtures of organic solvents.

The immunoglobulin preparation can also comprise excipients. As used herein the terms "excipient" refers to an inert substance which is added to the pharmaceutical composition. The excipients can be added into the preparation, for example, in order to ensure that the active ingredient retains its chemical stability and biological activity upon storage, to aid the manufacturing process and/or for aesthetic reasons e.g. color.

Examples of excipients include, but are not limited to, various sugars, such as maltose, sucrose or, D-sorbitol; glycine; polymeric excipients, such as PEG or serum proteins, such as albumin.

In one embodiment of the invention, the immunoglobulin preparation comprises from about 1.6 to about 2.6% glycine, such as about 2.25%, and 0.3% NaCl.

The immunoglobulin preparation can comprise a relatively high protein concentration. The range of protein concentration can be from about 5 to 25% w/v, from about 15 to 25% w/v, from about 14 to 20% w/v, or from about 14 to 18% w/v. In one embodiment of the invention, the preparation of the invention has a protein concentration of about 16% w/v. Advantageously, the preparation is well tolerated when administered subcutaneously. In one embodiment of the invention, at least 90%, for example about 91, 92, 93, 94, 95, 96, 97, 98 or 99% of the proteins in the preparation are human immunoglobulin G. The immunoglobulin preparation of the invention can contain equal to or less than 10% polymers and/or aggregates, for example, the polymer levels can be less than 3%. The content of monomers and/or dimers in the preparation can be equal or more than 85%. Optionally, the immunoglobulin preparation is adjusted to a physiological compatible value. The pH range can be between about 6.4 to about 7.2, for example about 6.4, 6.5, 6.6, 6.7, 6.8, 6.9, 7, 7.1 or 7.2. The pH of the preparation can be near neutral.

The method according to the invention can be used for preventing, treating, and/or reducing hepatitis B viral infection.

The term "treating" refers to curing, healing, alleviating, relieving, altering, remedying, substantially ameliorating, improving, or affecting a disease, disorder or condition associated with hepatitis B virus, or one or more symptoms thereof. As used herein, "preventing", and "prophylaxis" refers to reducing the risk or likelihood that the subject will acquire a disease, disorder or condition associated with hepatitis B virus. The term "reducing" refers to decreasing the progression or severity of the disease.

In one embodiment of the invention, the method is used to enhance the bioavailability of hepatitis B immunoglobulin when administered subcutaneously. In another embodiment of the invention, the method is used to prevent viral hepatitis B recurrence following orthotopic liver transplantation (OLT). In another embodiment of the invention, the methods of the invention are used for preventing viral hepatitis B in orthotopic liver transplantation (OLT) patients. In another further embodiment of the invention, the methods of the invention are used in a subject born to a hepatitis B viral infected mother. Yet, in another embodiment of the invention, the methods of the invention are used in a subject exposed to hepatitis B virus.

The present invention provides a method for preventing hepatitis B viral infection recurrence in a subject who underwent orthotopic liver transplantation. The method comprises administering subcutaneously to the subject an anti-hepatitis B immunoglobulin preparation. In one embodiment of the invention the administering comprises a maintenance dose which is higher than the intramuscular dose, thereby achieving anti-hepatitis B antibodies in the circulation of the subject at a similar level and timing as in the intramuscular route.

In one embodiment of the invention, the required maintenance subcutaneous dose is at least 1.5-fold, such as about 2 or 2.5 fold the applied maintenance intramuscular dose as exemplified above.

The immunoglobulin preparation can comprise anti-hepatitis B antibodies at a titer of greater than 635 IU/ml such as about 700, 1000, 1400, and 2000 IU/ml.

Subject matter of the present invention embraces an immunoglobulin preparation for subcutaneous administration as specified above. The immunoglobulin preparation contains hepatitis B antibodies which react with the surface antigen(s) or determinant(s) of the virus and destroys and/or inhibits its infectivity and virulence. The immunoglobulin preparation can be used in a subject pre or post OLT due to a liver disease caused by hepatitis B viral infectiuon.

The immunoglobulin preparation of the invention can be prepared from blood or blood fractions donated by healthy, screened donors with high titers of anti-hepatitis B antibodies. Example of such a technique is disclosed in WO-2007/017859 which content is incorporated herein by reference. The blood or blood fraction can be human or of non-human source.

The term "blood fraction" refers to a fraction of whole blood which comprises immunoglobulins such as plasma or serum.

The cut-off value of the blood or blood fraction can be 40 IU/ml. In one embodiment of the invention, the cut-off value is 50 IU/ml. In another embodiment of the invention, the cut-off value is 80 IU/ml. A "cutoff" value is the minimum value of blood fraction sample which is considered as a high titer; thus being suitable for manufacturing the immunoglobulin preparation of the invention.

The presence of anti-hepatitis B antibodies in the blood sample can be measured by a variety of known methods, such as biochemical assays or biological assays.

In one embodiment of the invention a bioassay such as plaque reduction neutralization tests (PRNTs) can be used in order to determine the antibody levels. The term PRNT refers to a reduction in plaque counts, e.g. a PRNT50 titer is based on a 50% or greater reduction in plaque counts. The assay can be performed in an in-vitro setting in various cell types. In another embodiment of the invention a biochemical assay such as Enzyme-Linked Immunosorbent Assay (ELISA) is carried out in order to determine the antibody levels. Several variations of ELISA testing can be used, including, but not limited to, indirect ELISA, sandwich ELISA, and competitive binding. Also, an automated ELISA system can be used, for example by using an automated instrument, in order to allow multiple screening.

The plasma pool can be treated to reduce and/or inactivate infective particles. This can be carried out by different methods such as, but no limited to, filtration, solvent/detergent treatment, heat treatment, such as pasteurization, gamma or UVC (<280 nm) irradiation, or by any other method known in the art.

The term "infective particle" refers to a microscopic particle, such as, but not limited to, a microorganism or a prion, which can infect or propagate in cells of a biological organism. The infective particles are for example viral particles.

The inactivation procedure of infective particles can be carried out by adding an inactivating molecule to the composition prior to and/or during the procedure. The added molecules and their products can be removed by gravitation, column chromatography, phase separation or by any other method known in the art. The removal of infective particles can be carried out by filtration or by selective absorption methods such as affinity, ion exchange or hydrophobic chromatography. A multi-step viral inactivation procedure can be carried out. For example, the composition can be subjected to solvent/detergent treatment, heat treatment, selective chromatography and filtration. Examples of immunoglobulin purification techniques are disclosed in U.S. Pat. No. 6,468,733, EP patent No. 1,161,958 and International PCT Publication WO99/18130 whose contents are incorporated by reference. For example, a method for the purification of immunoglobulins from a source solution such as Cohn Fraction II may comprise: (a) pre-treating a cation exchange resin with an acidic solution having a pH of 4.0-4.5; (b) contacting the source solution with the cation exchange resin; and (c) eluting the immunoglobulins bound to the cation exchange resin. Prior to contact with the cation exchange resin, the source solution may be treated with an organic solvent and detergent.

The immunoglobulin preparation can be concentrated by ultra-filtration process. The ultrafiltration can be followed by diafiltration to exchange the buffer. The concentration and dialysis by ultrafiltration and diafiltration, respectively, can be performed in one step or as two separate steps. The diafiltration can be carried out against any solution which is suitable for subcutaneous injection. Non limiting examples of such solutions include, but are not limited to, 0.3% NaCl and from about 1.6 to about 2.6% glycine such as about 2.25%.

Regular monitoring of serum hepatitis B antigen such as hepatitis B surface antigen (HBsAg) and/or levels of anti-hepatitis B antibody following administration of the immunoglobulin preparation can be carried out to track treatment response and allow for treatment adjustment. The antibody levels can be determined by a variety of methods as indicated above and hepatitis B antigen presence in the circulation can be determined using techniques well known in the art such as an ELISA procedure as indicated above. In one embodiment of the invention, the response to the therapy is examined by monitoring the serum HBV DNA levels. In another embodiment of the invention, the response is examined by monitoring loss of hepatitis e antigen (HBeAg) in patients who were initially HBeAg positive. Alternatively, liver function tests can be carried out to assess treatment response such as measuring alanine transaminase (ALT) serum levels.

The immunoglobulin preparation according to the invention can be provided in a vial or pre-filled syringe. The immunoglobulin preparation can be stored in either a liquid or in a solid form, e.g. as lyophilized powder. The preparation can be stored at a temperature of 4° C. The preparation of the invention may be used, for example, for passive immunization of subjects pre or post liver transplantation such as for prophylaxis of patients who underwent orthotopic liver transplantation, for passive immunization of individuals who are at increased risk of infection with hepatitis B virus such as, but not limited to, babies born to a hepatitis B viral infected mother, subject exposed to HBV, for example, by parenteral exposure (e.g., accidental "needle stick" of a health care worker), direct mucous membrane contact (e.g., accidental splash), or oral ingestion (e.g., pipetting accident) involving hepatitis B-infected material such as blood, plasma or serum.

The immunoglobulin preparation can also be used as prophylaxis in subjects who are unable to develop adequate immune protection and who are exposed to continual risk of infection, e.g. dialysis patients, patients receiving multiple transfusion or blood components.

Following exposure to blood containing HBsAg the immunoglobulin can be given as soon as possible after the exposure. For example, the immunoglobulin preparation can be administered within 7 days following the exposure, for example, 24 hours following the exposure.

The immunoglobulin preparation of the invention may also be used in a method for diagnosing a HBV-infected subject. This can be carried out by obtaining a body fluid sample, such as a blood sample, a lymph sample or any other body fluid sample, from said subject and contacting it with the preparation of the invention under conditions which allow the formation of antibody-antigen complex as known in the art. Detection of the antibody-antigen complex level can be carried out by any methods known in the art. Negative control samples can also be tested. Each sample which is significantly higher than the control sample indicates on an HBV infected subject.

The present invention also provides kits comprising containers comprising the immunoglobulin preparation according to the invention. The kit can also contain instructions for use to the physician, health care professional, or the patient. The containers can be vials or pre-filled syringes which contain the preparation of the invention. The immunoglobulin can be provided in the kit as a solution or in a solid form, e.g. as lyophilized powder. The lyophilized powder can be reconstituted with injectable carries. The container can be of different sizes and contain different volumes of the preparation, for example, the preparation can have a volume of equal to or less than about 5 ml, for example, about 3, 2, 1.5 or 1 ml. The kit may also contain a separate vial of the injectable carrier. In one embodiment of the invention, the reconstituted immunoglobulin comprises more than 635 IU/ml such as 700, 1000, 1400, and 2000 IU/ml. Optionally, a syringe of an appropriate size is also included in the kit. Such a kit can contain the monthly dosage divided into several vials containing the required dose, for example, the kit can contain 2 vials with a total dosage to be administered every second week.

The immunoglobulin preparations, methods and kits according to the present invention have at least one of the following advantages: facilitates ambulatory care such as home therapy (self administration) thereby improving the patient's life quality, has a high safety profile with very few local or systemic adverse effects, attains an adequate concentration of circulating antibodies more rapidly as compared to other known subcutaneous formulations, provides good protection or treatment against HBV, enables fast administration, allows less frequent injections per month as compared to other available formulations, can be administered in a small volume dose, and reduces health care services and patients costs.

Yet another object of the invention is accomplished by providing a method for treating, preventing and/or reducing hepatitis B viral infection in a subject in need. The method comprises: a) providing an anti-hepatitis B immunoglobulin preparation, and b) administering subcutaneously to the subject the preparation of a) in a dose higher than that applied by the intramuscular route to achieve anti-hepatitis B antibodies in the circulation of the subject at a similar level and timing as the intramuscular route. In one embodiment of the invention, the immunoglobulin preparation is as defined above.

In one embodiment of the invention, the subcutaneous dose is at least 1.5-fold higher than the applied by intramuscular dose.

In another embodiment of the invention, the subject was previously treated by intravenous HBIG administration.

In another further embodiment of the invention, the anti-hepatitis B antibodies level attained in the circulation of the subject is about or greater than 100 mIU/ml, like for example 150, 200, 400 or 500 mIU/ml. In one embodiment of the invention, the anti-hepatitis B antibodies level attained in the circulation of the subject is higher than 100 mIU/ml.

The proposed method can be carried out pre or post orthotopic liver transplantation, as prophylactic treatment to prevent viral hepatitis B recurrence in a liver transplant recipient, in a subject born to a hepatitis B viral infected mother or in a subject who was exposed to hepatitis B virus.

The immunoglobulin preparation according to the present invention can be administered in the dose and volumes as defined above.

In one embodiment of the invention, the therapeutic responses following subcutaneous administration according to the invention are comparable to those induced by the intramuscular administration. The term "comparable therapeutic response" means that the use of subcutaneous administration according to the invention has substantially the same therapeutic response and/or prophylactic effect, as defined herein above, as the intramuscular administration.

It is another object of the present invention to provide a pharmaceutical composition for subcutaneous treatment of OLT patients comprising a pharmaceutically acceptable carrier and a dose of anti-hepatitis B immunoglobulin which is higher than the dose in a pharmaceutical composition formulated for intramuscular treatment of the same indication. The term "indication", as used herein, refers to a medical condition or symptoms associated with a medical condition, such as, but not limited to, a disease, disorder or condition associated with hepatitis B virus, pre or post orthotopic liver transplantation, perinatal exposure of infants born to a hepatitis B viral infected mother and/or following exposure to hepatitis B virus.

In one embodiment of the invention, the subcutaneous dose is at least 1.5-folds higher, e.g. about 2 or 2.5-folds, than the intramuscular dose.

In another aspect, the invention provides a method for treating, preventing and/or reducing a disease, disorder or condition associated with hepatitis B virus in a subject in need thereof, the method comprising a first dosing regimen of intramuscular administration of anti-hepatitis B immunoglobulin, followed by a second dosing regimen, which comprises subcutaneously administering to the subject a dose of anti-hepatitis B immunoglobulin that is higher than the dose employed by the first dosing regimen of intramuscular administration, thereby obtaining anti-hepatitis B antibodies in the circulation of the subject at a similar level and timing as in the first dosing regimen of intramuscular administration.

In one embodiment of the invention, the timing is before the third, second or first day following subcutaneous administration.

In one embodiment of the invention, such transitioning can be carried out in situations wherein intramuscular doses of HBIG are contra-indicated.

In the methods of the invention, the immunoglobulin preparation according to the invention can be administered in combination with one or more agents. Such agents may include, as non limiting example, anti hepatitis B monoclonal antibodies, anti-viral agents, nucleoside analogs, inhibitors of DNA polymerase, interferons such as interferon alpha-2a, adefovir dipivoxil, lamivudine (Epivir-HBV), adefovir (Hepsera), entecavir (Baraclude), telbivudine (Tyzeka), tenofovir (Viread) and the like.

In the case of such a combination therapy the antiviral agents can be provided simultaneously with the immunoglobulin preparation or sequentially either before or after treatment with the immunoglobulin preparation. In one embodiment of the invention, the antiviral agent and the immunoglobulin preparation are formulated together and administered simultaneously. In another embodiment of the invention, the antiviral agent can be administered as a separate component either before or after treatment with the immunoglobulin preparation. The antiviral agent can be administered in any suitable and/or conventional mode, including, but not limited to, orally, topically, intravenously, intramuscularly and subcutaneously. The antiviral agent can be used in a dosing which allows optimizing the efficacy of the treatment. In this regard, the desired anti-hepatitis B antibodies in the circulation can be lower compared to a non combined treatment.

If desired, the immunoglobulin preparation of the invention can be administered in combination with hepatitis B active vaccine such as with a live attenuated virus vaccine. Advantageously, such combination treatment may develop a greatest degree of protection against hepatitis B viral infection. The vaccine can be administered either before or after treatment with the immunoglobulin preparation. The vaccine can be administered in a different location than the administered immunoglobulin preparation. In one embodiment of the invention, the hepatitis B active vaccine is administered after treatment with the immunoglobulin preparation. In one embodiment of the invention, the hepatitis B active vaccine is administered before treatment with the immunoglobulin preparation.

In one embodiment of the invention any hepatitis B immunoglobulin preparation is used and administered SC at a dose that is 1.5 fold higher than that required by the intramuscular route. In one embodiment of the invention when converting the intramuscular dosing to the subcutaneous dosing the dose is increased by 50%.

The disclosure of applications, patents and publications, cited above or below, is hereby incorporated by reference.

The following examples are illustrative but not limiting.

EXAMPLES

Materials and Methods

Antibody analysis: anti-hepatitis B surface antigen (Anti-HBs) antibodies were analyzed by the automated immunoassay analyzer (AxSYM system; Abbott Diagnostics) using AUSAB kit [Microparticle Enzyme Immunoassay (META), Abbott Diagnostics (Abbott AxSYM® HBsAg Assay)].

Animal models: Two models were used as specified below. The study procedures were reviewed and approved by the Committee for Ethical Conduct in the Care and Use of Laboratory Animals, at the Hebrew University, Jerusalem, Israel.

In both models the animals were housed for acclimation for at least 5 days before surgical procedures. Animals were provided diet ad libitum and had free access to drinking water.

At the end of the study, surviving animals were euthanized by $CO_2$ asphyxiation.

Rabbit model: Female NZW rabbits (Harlan Biotech, Israel, LTD), weighing about 3 kg at study initiation were used. Four groups of rabbits were used (4 rabbits per group). The constitution of the tested groups and the pharmacokinetic parameters are listed in Table 1 below.

Test items: HepB IG 16% preparation containing anti-HBs antibodies at a titer of 1,400 IU/ml served as source material for all tested items. HepB IG 16% was diluted in 5% regular IVIG and 10% maltose to produce a final 5% IgG preparation for IV administration. For SC/IM administration the source material was diluted in concentrated IVIG (20%) and glycine/saline diluent (2.25% glycine, 0.3% NaCl; at a pH of 6.5-7.0) to produce a final 16% IgG preparation. Concentration and diafilteration were carried out using Filtron, Minisette 30K.

The 5% and 20% IVIG preparations used to dilute the source material contained negligible titers of anti-HBs antibodies. The final diluted test items which were used for injection contained 109 and 565 IU/ml anti-hepatitis B antibodies for the IV and the SC/IM solutions respectively (see Table 1). The antibody titer was measured using the Abbott AxSYM® HBsAg assay according to manufacturer's instructions.

The test items were administrated at room temperature by one of the following routes:
(i) Intravenous (IV) slow injection (about 1-2 ml/min; 1.8 ml/kg) through the ear vein followed by flushing with heparinised saline.
(ii) Subcutaneous (SC) injection (0.3 ml/kg) divided between two sites (back of the neck).
(iii) Intramuscular (IM) injection (0.3 ml/kg) divided between two sites (thighs).

Animals in the IV groups were tranquilized by xylazine 2% while introducing the test item.

Body weights were taken periodically and the animals were monitored for local adverse events at the injection sites.

TABLE 1

Constitution of test groups.

| Test Item | Route | Volume and Dosage | IU/kg |
|---|---|---|---|
| HepB IG 5% | IV | 1.8 ml/kg, 109 IU/ml | 196.2 |
| HepB IG 16% | SC IM | 0.3 ml/kg, 565 IU/ml | 169.5 |
| Glycine/*NS | SC | 0.3 ml/kg | — |

*NS—normal saline.

Blood samples: Pre-treatment bleeding was obtained from the ear using standard techniques. The blood from the IV treated animals was taken from the contra-lateral ear that was not used for the IV administration. About 0.5 ml of blood was collected at each time point. The measurements were carried out in the following time points 2, 6 and 8 hours and 1, 2, 3, 4, 5, 6, 7 and 14 days following administration. Serum was separated by centrifugation at 2500 g for 15 minutes at room temperature and transferred into a new tube for storage at −18° C. or below until assayed.

Cannulated rat model: Male HsdHan wistar rats (Harlan Biotech Israel Ltd) at the age of about 9-10 weeks and weighing 300 g at study initiation were used in this model (4 rats per group).

All surgical procedures were done under analgesia (Buprenorphine, S.C., 0.05 mg/kg) and anesthesia (induced by inhalation of 4% Isoflurane in oxygen and maintained with 1.0-2.0% Isoflurane).

In each of the animals external jugular vein was catheterized and the catheter was secured in the vein with the aid of ligatures. The catheter was then passed through a subcutaneous tunnel created by blunt dissection towards the skin on the dorsal aspect between the scapulas and secured by sutures or stainless steel wound clips.

Body weights were measured during acclimation, shortly before anesthesia induction towards cannulation, prior to dosing and on 2, 4, 7 and 15 days post-dosing.

Test items: 5% and 16% HepB IG preparations were prepared as indicated above. The final diluted test items used for injection contained 109 and 282 IU/ml anti-hepatitis B antibodies for the IV and the SC/IM solutions respectively (see Table 2 below).

The test items were administered about twenty-four hours after Jugular cannulation. The constitution of the tested groups and the pharmacokinetic parameters are listed in Table 2. The test items were administrated at room temperature in one of the following routes:

(i) Intravenous (IV) bolus injection (1.8 ml/kg) through the cannula (jugular), followed by flushing with 0.2 ml of warmed saline.
(ii) Subcutaneous (SC) injection (0.6 ml/kg) over the left flank of the animal.
(iii) Intramuscular (IM) injection (0.6 ml/kg) divided between two sites to the right and the left thigh muscles of the animal.

TABLE 2

Constitution of test groups.

| Test Item | Treatment Route | Volume and Dosage | IU/kg |
|---|---|---|---|
| HepB IG 5% | IV | 1.8 ml/kg, 109 IU/ml | 196.2 |
| HepB IG 16% | SC IM | 0.6 ml/kg, 282 IU/ml | 169.2 |

Blood samples: Pre-treatment bleeding point was obtained from the retro-orbital sinuses, under isoflurane anesthesia. After dosing, blood samples were obtained via the intravenous cannula, as long as the cannula was potent. About 0.25-0.3 ml of blood was collected at each time point. Following each blood collection from the cannula about 0.3 ml of warmed physiological saline was injected. Alternatively, blood samples were obtained from the retro-orbital sinuses or by tail sectioning under general Isoflurane anesthesia. The measurements were carried out in the following time points 1, 2, 4, 7 and 11 days following administration. At the final bleeding, day 15 post-dosing, blood was collected by cardiac puncture, under general anesthesia. The blood sample was put into a tube containing 1 μl of Sodium Heparin (5000 IU/ml). Each vial was gently mixed and plasma was separated by centrifugation at 2500 g for 10 minutes at room temperature and transferred into a new tube for storage at −18° C. or below until assayed.

Example 1

Monitoring the Anti-Hepatitis B Antibody Levels in the Circulation Following Intravenous, Subcutaneous or Intramuscular Administration of Hepatitis B Immunoglobulin The present example was aimed to determine the level of circulating antibodies following the different routes of administrations. Two animal models were used in these experiments: a rabbit model and cannulated rat model. In each model the animal was administered with the different test items as indicated in Table 1 or 2 and blood samples were taken for analysis of anti-hepatitis B antibody levels (as specified above). Each determination is the average result of four animals.

FIG. 1 shows the recovery of anti-hepatitis B antibodies in the rabbit's blood following administration of HBIG in the different routes of administrations. The level of antibodies on day one following IV administration was assigned as a reference value (100%).

The results indicate that both IV and IM administration resulted in a high and rapid appearance of anti-hepatitis B antibodies in the animal's circulation at day 1. IM administration achieved a maximum antibody level of about 70-80% of the IV level one day following administration. In contrast, SC administration resulted in a delayed appearance of antibodies in the blood. About 35% of the IV level was attained one day following administration and a peak serum concentration of 53% was observed 3 days following administration.

Figure 2:
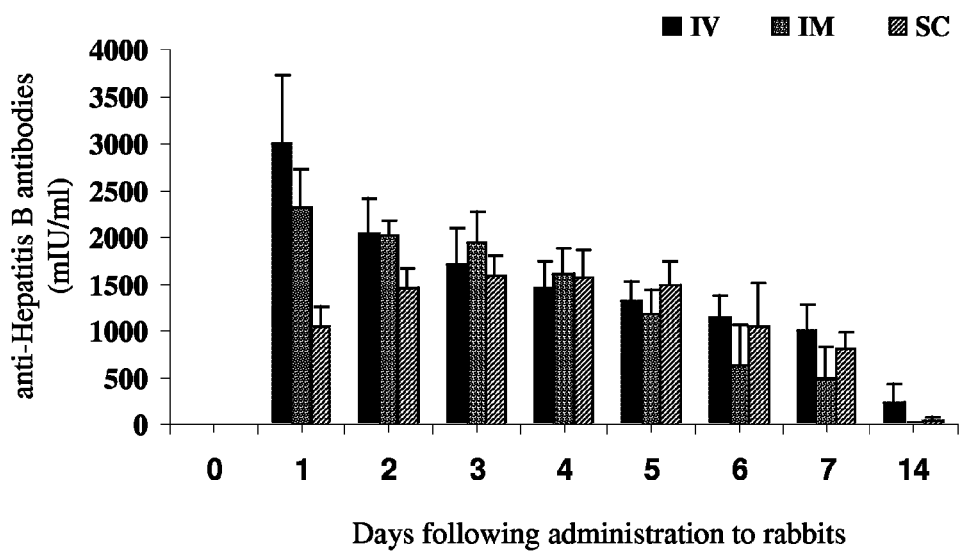
FIG. 2: shows the level of the anti-hepatitis B antibodies in rabbit's blood during the first two weeks following administration of HBIG. The immunoglobulin was administered by IV, IM or SC route.

FIG. 2 shows the level of the anti-hepatitis B antibodies in the rabbit's blood during the first two weeks following administration of the HBIG preparation. It is apparent that the antibody levels in the circulation in both IV and IM routes is substantially higher than that observed in the SC group on the first and second days following administration (2998 for IV and 2305 for IM compared with 1040 mIU/ml, for SC on day 1 following administration and 2032 for IV and 2016 for IM compared with 1460 for SC mIU/ml, on day 2 following administration).

Figure 3:
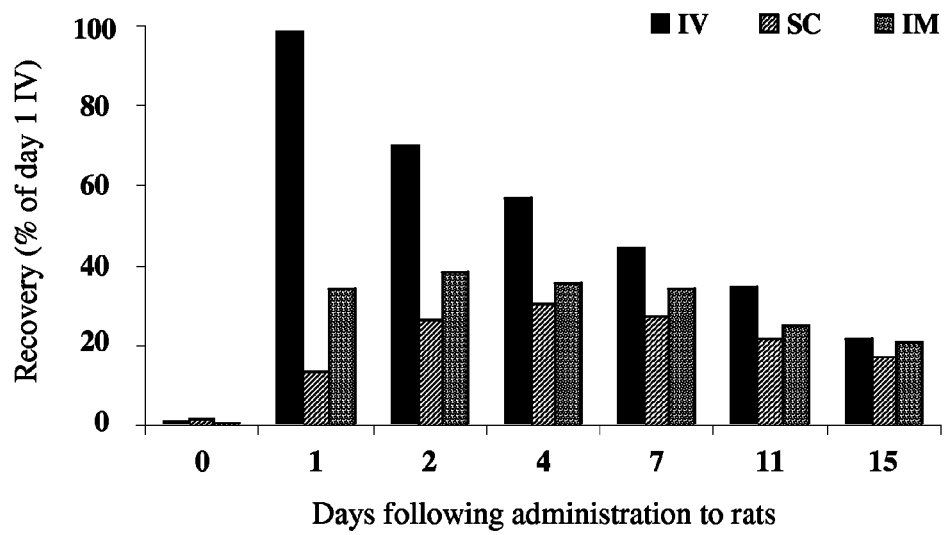
FIG. 3: shows the recovery of anti-hepatitis B antibodies in rat's blood following administration of HBIG. The immunoglobulin was administered by IV, IM or SC route. The results are presented as percentage of the level of antibodies on day one following IV administration (100%).

Similar results were found in the cannulated rat model. FIG. 3 shows the recovery of anti-hepatitis B antibodies in the rat's blood following administration of HBIG. The results are presented as percentage of the level of antibodies on day one following IV administration (100%).

As observed in the rabbit model, in the IV and IM route the anti-hepatitis B antibodies appear more rapidly than when given subcutaneously. 34 and 38% of the IV level was attained on day 1 and 2 following administration, respectively, for IM vs. 13 and 27% antibody recovery on day 1 and 2 following administration, respectively, for SC administration (FIG. 3). SC injection exhibited a peak serum concentration of about 30% about 4 days following administration.

Figure 4:
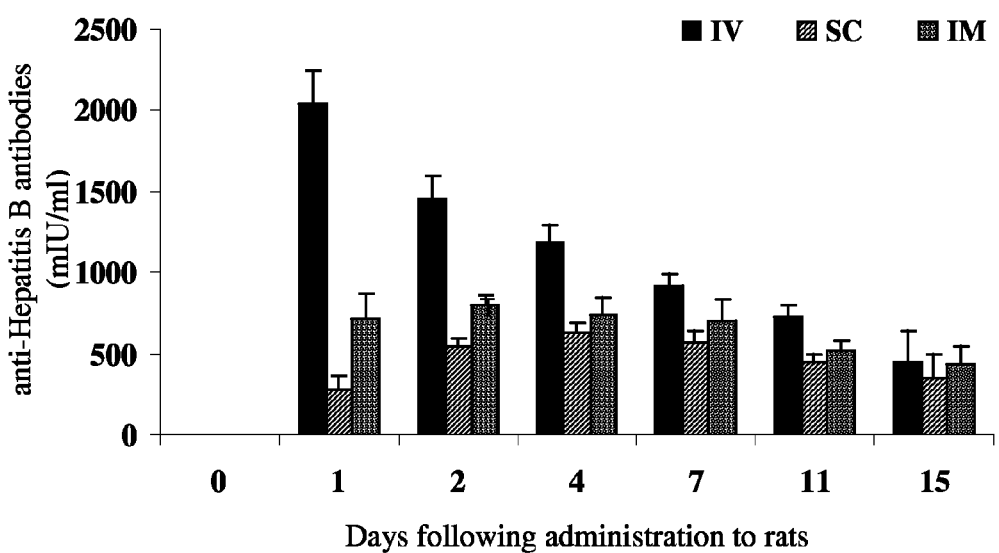
FIG. 4: shows the anti-hepatitis B antibody levels in rat's blood during 15 days following administration of HBIG. The immunoglobulin was administered by IV, IM or SC route.

While observing the antibody levels in the rat's circulation during the first two weeks following administration (FIG. 4) it is evident that SC administration results in a lower antibody level in the blood on day 1 and 2 following injection as compared to IM and IV administration (279 compared with 2042 and 714 for SC, IV, and IM respectively, on day 1 following administration and 549 compared with 1445 and 795 mIU/ml for SC, IV, and IM respectively, on day 2 following administration).

The results obtained herein collected during the observation period of two weeks show that the calculated average area under the curve (AUC) in both models was similar in the SC and IM routes. These results are in line with previous reports (Thürmann et al. 2006 and Hooman at al. 2008).

In addition, it is apparent that in both models intramuscular administration resulted in about 2-fold increase in circulating anti-hepatitis B antibodies one day following injection as compared to subcutaneous administration (2305/1040 and 714/279 for the rabbit model or cannulated rat model, respectively).

No adverse events occurred at the injection sites during the study period in both animal models.

The above results indicate that as opposed to IV and IM, SC administration is slowly released into the intravascular space with peak serum concentrations achieved 3 to 4 days after injection, i.e. administering an immunoglobulin composition in SC route results in a decreased intravenous bioavailability on the first two days following injection as compared to the two other routes of administration. When comparing the anti-hepatitis B antibodies in the circulation on day one following administration, it is evident that IM administration lead to about 2-fold increase in the antibody levels as compared to SC administration. This indicates the advantage of administering subcutaneously a higher amount of antibodies compared to intramuscular injection, since administering this amount will result in early adequate serum IgG levels.

The invention claimed is:
1. A method for subcutaneous immunoglobulin hepatitis B therapy, comprising subcutaneously administering to a subject in need a dose of anti-hepatitis B immunoglobulin that is at least 2-fold higher than a dose of anti-hepatitis B immuno- globulin administered by the intramuscular route, thereby achieving anti-hepatitis B antibodies in the circulation at a similar level and timing as by the intramuscular route, wherein said subcutaneous dose is higher than 2170 IU and the administration of the immunoglobulin is carried out in the body in an anatomic site selected from the group consisting of the arm, the abdomen, and the front of the thigh.

2. The method according to claim 1, wherein said subject is selected from the group consisting of an orthotopic liver transplantation (OLT) patient, a newborn to a hepatitis B virus infected mother, and a subject exposed to the virus.

3. The method according to claim 1, wherein said subcutaneous dose is equal to or higher than 3000 IU.

4. The method according to claim 1, wherein said subcutaneous administering is carried out by injection.

5. The method according to claim 1, wherein said subcutaneous administering is carried out by a single dispensation.

6. The method according to claim 1, wherein said subcutaneous dose has a titer of anti-hepatitis B antibodies that is greater than 635 IU/ml.

7. A method for treating hepatitis B virus infection, comprising administering to a subject in need thereof a dose of anti-hepatitis B immunoglobulin sufficient to obtain a predetermined level of anti-hepatitis B antibodies in the circulation of said subject, the improvement wherein the anti-hepatitis B immunoglobulin is administered by the subcutaneous route in a dose that is at least 1.5 times higher than the intramuscular formulated dose needed to obtain said predetermined level of anti-hepatitis B antibodies in the circulation of said subject, wherein said predetermined level is obtained in the circulation by the subcutaneous dose at a similar timing as in said intramuscular formulated dose and wherein said subcutaneous dose is higher than 2170 IU and the administration of the immunoglobulin is carried out in the body in an anatomic site selected from the group consisting of the arm, the abdomen, and the front of the thigh.

8. The method according to claim 7, wherein said predetermined level of anti-hepatitis B antibodies in the circulation is greater than 100 mIU/ml.

9. The method according to claim 7, wherein said timing is before the third, second or first day following subcutaneous administration.

10. The method according to claim 7, wherein said subcutaneous administration is carried out by injection.

11. The method according to claim 7, wherein said subcutaneous administration is carried out by a single dispensation.

12. The method according to claim 7, wherein said subject was previously treated by a dosing regimen of intravenous administration of anti-hepatitis B immunoglobulin.

13. The method according to claim 7, wherein said subcutaneous dose has a titer of anti-hepatitis B antibodies that is greater than 635 IU/ml.

14. A method for preventing hepatitis B viral infection recurrence in a subject who underwent orthotopic liver transplantation (OLT), comprising administering to said subject a dose of anti-hepatitis B immunoglobulin sufficient to obtain a predetermined level of anti-hepatitis B antibodies in the circulation of said subject, the improvement wherein the anti-hepatitis B immunoglobulin is administered by the subcutaneous route in a dose that is at least 1.5 times higher than the intramuscular formulated dose needed to obtain a similar level of anti-hepatitis B antibodies in the circulation of said subject, wherein said predetermined level is obtained in the circulation by the subcutaneous dose at a similar timing as in said intramuscular formulated dose and wherein said subcutaneous dose is higher than 2170 IU and the administration of the immunoglobulin is carried out in the body in an anatomic site selected from the group consisting of the arm, the abdomen, and the front of the thigh.

15. The method according to claim 14, wherein said subcutaneous administering is carried out by injection.

16. The method according to claim 14, wherein said subcutaneous administering is carried out by a single dispensation.

\* \* \* \* \*